United States Patent [19]

Huang et al.

[11] Patent Number: 5,262,537
[45] Date of Patent: Nov. 16, 1993

[54] DERIVATIVES OF 4,5,6,7-TETRAHYDROIMIDAZO-[4,5-C]PYRIDINYL-6-CARBOXYLIC ACID

[75] Inventors: Bao-Shan Huang, Edison; Danging D. Feng, Branchburg Township, Somerset County; Martin Gall, Morris Township, Morris County; Suzanne M. Evans, Springfield; Vidyadhar M. Paradkar; Raghunathan V. Nair, both of Basking Ridge; Tamara B. Latham, North Plainfield, all of N.J.

[73] Assignee: Anaquest, Inc., Liberty Corner, N.J.

[21] Appl. No.: 33,522

[22] Filed: Mar. 19, 1993

[51] Int. Cl.$^5$ ............... A61K 31/445; A61K 31/415; C07D 471/04; C07D 471/10
[52] U.S. Cl. ........................................ 546/118; 546/15
[58] Field of Search ................ 546/15, 118; 514/278, 514/303

[56] References Cited

U.S. PATENT DOCUMENTS 4,977,175 12/1990 Ohta et al. ........................... 514/394

*Primary Examiner*—C. Warren Ivy
*Assistant Examiner*—D. Margaret M. Mach
*Attorney, Agent, or Firm*—R. Hain Swope; Larry R. Cassett

[57] ABSTRACT

This invention pertains to a method for treating a condition of nausea and vomiting in a mammal which comprises administering a therapeutically effective amount of a 4,5,6,7-tetrahydroimidazo[4,5-c]pyridinyl-6-carboxylic acid derivative represented by the formula:

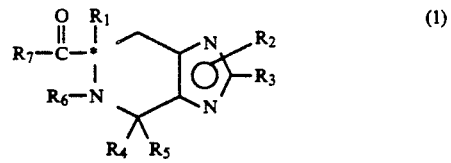

wherein $R_1$ and $R_2$ are hydrogen or lower-alkyl; $R_3$ is selected from the group consisting of hydrogen, lower-alkyl, nitro, amino, cyano, and alkylmercapto; $R_4$ and $R_5$ are selected from the group consisting of hydrogen, lower-alkyl, aryl, and aryl lower-alkyl, or $R_4$ and $R_5$ together with the carbon atom to which they are attached form a 5- or 6-member saturated hydrocarbon ring; $R_6$ is selected from the group consisting of hydrogen, lower-alkyl, aryl lower-alkyl, formyl, lower-alkyl carbonyl, and aryl carbonyl; $R_7$ is selected from the group consisting of phenyl, thienyl, indolyl, indazolyl, benzo[b]furanyl, benzo[b]thiophenyl, and $R_8R_9$—N—; $R_8$ is selected from the group consisting of 8-[1,2,3,4,-tetrahydroquinolinyl], pyridinyl, 3-quinolinyl, 2-naphthalinyl, 2-thiazolyl, 2-benzothiazolyl, 4-[2,1,3]benzothiadiazolyl, 2-(4,5,6,7-tetrahydrobenzo)thiazolyl, 7-(2,2-dimethyl-2,3-dihydrobenzo)furanyl, and phenyl; $R_9$ is hydrogen or lower-alkyl; $R_8R_9$—N— is selected from the group consisting of 1-indolinyl, 1-(3,3-dimethylindolinyl), and 1-(1,2,3,4-tetrahydroquinolinyl); wherein the groups represented by $R_7$ other than $R_8R_9N$— may be unsubstituted or substituted with one or more substituents selected from the group consisting of lower-alkyl, lower-alkoxy, di-lower-alkylamino, and aryloxy, and the groups represented by $R_8$ and the radical $R_8R_9N$— may have one or more substituents selected from the group consisting of hydroxy, halogen, lower-alkyl, lower-alkoxy, amino, mono- or di-lower-alkylamino, lower-alkyl carbonyl, lower-alkoxy carbonyl, and aryloxy; wherein each aryloxy group may be unsubstituted or substituted with substituents independently selected from the group consisting of lower-alkyl, lower-alkoxy, halogen, and trifluoromethyl with the proviso that, when $R_8$ is phenyl, said phenyl group contains at least one substituent.

21 Claims, No Drawings

DERIVATIVES OF 4,5,6,7-TETRAHYDROIMIDAZO-[4,5-C]PYRIDI-NYL-6-CARBOXYLIC ACID

FIELD OF THE INVENTION

This invention relates to derivatives of novel 4,5,6,7-tetrahydroimidazo[4,5-c]pyridinyl-6-carboxylic acid useful as potent and selective anti-emetic or anti-nausea agents, or both, for pre-operative, intra-operative, and post-operative use.

BACKGROUND OF THE INVENTION

Nausea and vomiting are a serious complication of surgery and certain areas of chemotherapy, particularly cancer treatment. Historically, dopamine receptor antagonists, such as droperidol or prochlorperazine, have been used to treat nausea and vomiting. These agents, however, tend to produce unwanted side effects such as prolactin release and sedation.

Recently, a new class of agents, characterized by their antagonism of serotonin at the 5-HT$_3$ receptor with little or no D$_2$ receptor antagonist properties, has been found to prevent or curtail emetic episodes caused by irradiation or chemotherapeutic agents such as cisplatin. These effects were potentiated by coadministration of dexamethasone. In addition, these 5-HT$_3$ antagonists are useful in the treatment of gastric motility, anxiety, migraine, psychiatric disorders, and memory impairment. Various analogs of these new agents were found to have effects at a new serotonin receptor which is coupled to adenylate cyclase, and which has been called the 5HT$_4$ receptor. Agents of this latter type are thought to be associated with promotility and, therefore, have potential utility in treating gastrointestinal dysfunctions such as reflux oesophagitis and gastric stasis.

United Kingdom patent application no. 2,158,440, discloses certain 4,5,6,7-tetrahydroimidazo[4,5-c]pyridinyl carboxylic amide derivatives useful as antiviral agents.

U.S. Pat. No. 4,977,175, issued to Ohta et al., discloses 4,5,6,7-tetrahydrobenzimidazole derivatives useful as antagonists of 5-HT$_3$ receptors.

U.S. Pat. No. 4,963,546, issued to North et al., discloses 3-substituted indole derivatives useful as antagonists of 5-HT$_3$ receptors.

SUMMARY OF THE INVENTION

This invention pertains to a method for treating a condition, such as nausea and vomiting mediated through 5-HT$_3$ receptors alone, or in combination with other mechanisms, which comprises administering to the mammal an amount, therapeutically effective to relieve the condition, of a derivative of 4,5,6,7-tetrahydroimidazo[4,5-c]pyridinyl-6-carboxylic acid represented by the formula:

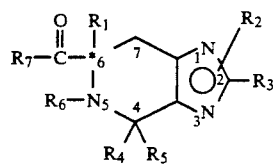

including optically active isomeric forms, and the pharmaceutically acceptable acid addition salts thereof, wherein:

$R_1$ and $R_2$ are hydrogen or lower-alkyl;

$R_3$ is selected from the group consisting of hydrogen, lower-alkyl, nitro, amino, cyano, and alkylmercapto;

$R_4$ and $R_5$ are independently selected from the group consisting of hydrogen, lower-alkyl, aryl, and aryl lower-alkyl, or $R_4$ and $R_5$ together with the carbon atom to which they are attached form a 5- or 6-member saturated hydrocarbon ring;

$R_6$ is selected from the group consisting of hydrogen, lower-alkyl, aryl lower-alkyl, formyl, lower-alkyl carbonyl, and aryl carbonyl;

$R_7$ is selected from the group consisting of phenyl, thienyl, indolyl, indazolyl, benzo[b]furanyl, benzo[b]thiophenyl, and $R_8R_9$—N—; and $R_8$ is selected from the group consisting of 8-(1,2,3,4,-tetrahydroquinolinyl), pyridinyl, 3-quinolinyl, 2-naphthyl, 2-thiazolyl, 2-benzothiazolyl, 4-[2,1,3]benzothiadiazolyl, 2-(4,5,6,7-tetrahydrobenzo)thiazolyl, 7-(2,2-dimethyl-2,3-dihydrobenzo)furanyl, and phenyl;

$R_9$ is hydrogen or lower-alkyl;

$R_8R_9$—N— is a radical selected from the group consisting of 1-indolinyl, 1-(3,3-dimethylindolinyl), and 1-(1,2,3,4-tetrahydroquinolinyl); wherein the groups represented by $R_7$ other than $R_8R_9N$— may be unsubstituted or substituted with one or more substituents selected from the group consisting of lower-alkyl, lower-alkoxy, di-lower-alkylamino, and aryloxy, and the groups represented by $R_8$ and the radical $R_8R_9N$— may have one or more substituents selected from the group consisting of hydroxy, halogen, lower-alkyl, lower-alkoxy, amino, mono-or di-lower-alkylamino, lower-alkyl carbonyl, lower-alkoxy carbonyl, and aryloxy, wherein each aryloxy group may be unsubstituted or substituted with one or more substituents independently selected from the group consisting of lower-alkyl, lower-alkoxy, halogen, and trifluoromethyl;

wherein the symbol * represents an asymmetric carbon atom at position 6 which may be in the R or S configuration, and each lower-alkyl group contains from 1 to 6 carbon atoms.

This invention also includes novel compounds within the scope of those represented by formula (I) and methods for their preparation. This invention relates also to methods for preparing and using the 4,5,6,7-tetrahydroimidazo[4,5-c]pyridinyl-6-carboxylic acid derivatives and the pharmaceutical compositions in which they may be employed.

DETAILED DESCRIPTION OF THE INVENTION

The derivatives of 4,5,6,7-tetrahydroimidazo[4,5-c]pyridinyl-6-carboxylic acid of the present invention block the emetic response induced by cytotoxic agents such as cisplatin or radiation and are therefore useful in the treatment of nausea and vomiting generally associated with cancer therapy. The subject compounds are also useful for treating patients experiencing post-operative emesis produced by anesthetics and/or adjunct drugs used in such procedures.

Many of the subject compounds are potent and selective antagonists of the neuronal 5-HT$_3$ receptor. However, the most potent of the subject anti-emetics do not necessarily have the highest affinity to the 5-HT$_3$ receptor. Therefore, the pharmacology of the subject compounds is not explainable simply on the basis of current knowledge of the role of 5-HT$_3$ antagonists in the treatment of nausea and vomiting.

The method of the present invention for treating a condition of nausea and vomiting in a mammal mediated through 5-HT$_3$ receptors alone, or in combination with other mechanisms, comprises administering to the mammal an amount, therapeutically effective to relieve the condition, of a 4,5,6,7-tetrahydroimidazo[4,5-c]pyridinyl-6-carboxylic acid compound represented by the general formula (1):

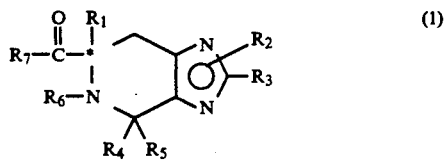

including optically active isomeric forms, and the pharmaceutically acceptable acid addition salts thereof. The symbol * represents an asymmetric carbon atom at position 6 which may be in the R or S configuration, and preferably is in the S configuration. Groups R$_1$ through R$_7$ are defined as set forth below.

In formula (1), R$_1$ and R$_2$ are individually hydrogen or lower-alkyl, preferably, hydrogen or methyl, and more preferably, hydrogen. R$_2$ may be attached to the nitrogen atom at position 1 or position 3 in the imidazole ring.

R$_3$ is selected from the group consisting of hydrogen, lower-alkyl, nitro, amino, cyano, and alkylmercapto, preferably, hydrogen, lower-alkyl, nitro, and amino, more preferably, hydrogen and methyl, and most preferably, hydrogen.

R$_4$ and R$_5$ are independently selected from the group consisting of hydrogen, lower-alkyl, aryl, and aryl lower-alkyl, or R$_4$ and R$_5$ together with the carbon atom to which they are attached form a 5- or 6-member saturated hydrocarbon ring. Preferably, R$_4$ and R$_5$ are selected from the group consisting of hydrogen and methyl, and more preferably, R$_4$ and R$_5$ are methyl.

R$_6$ is selected from the group consisting of hydrogen, lower-alkyl, aryl lower-alkyl, formyl, lower-alkyl carbonyl, and aryl carbonyl, preferably, hydrogen and methyl, and more preferably, methyl.

R$_7$ is selected from the group consisting of phenyl, thienyl, indolyl, indazolyl, benzo[b]furanyl, benzo[b]thiophenyl, and the radical R$_8$R$_9$—N—. In one embodiment, R$_7$ is selected from the group consisting of phenyl, thienyl, indolyl, indazolyl, benzo[b]furanyl, and benzo[b]thiophenyl. Preferably, R$_7$ is selected from the group consisting of phenyl, 2-thienyl, 3-thienyl, 2-indolyl, 3-indolyl, 3-indazolyl, 2-benzo[b]furanyl, 3-benzo[b]furanyl, 2-benzo[b]thiophenyl, and 3-benzo[b]thiophenyl, more preferably, R$_7$ is selected from the group consisting of 3-indolyl, 3-indazolyl, and 2-benzo[b]thiophenyl, and most preferably, R$_7$ is 2-benzo[b]thiophenyl.

In another embodiment, R$_7$ is R$_8$R$_9$—N— wherein R$_8$ is selected from the group consisting of 8-[1,2,3,4-tetrahydroquinolinyl], 3-pyridinyl, 3-quinolinyl, 2-naphthalinyl, 2-thiazolyl, 2-benzothiazolyl, 4-[2,1,3]benzothiadiazolyl, 2-(4,5,6,7-tetrahydrobenzo)thiazolyl, 7-(2,2-dimethyl-2,3-dihydrobenzo)furanyl, and phenyl. Preferably, R$_8$ is selected from the group consisting of 8-[1,2,3,4,-tetrahydroquinolinyl], 2-pyridinyl, 3-pyridinyl, 3-quinolinyl, 2-naphthalinyl, 2-thiazolyl, 2-benzothiazolyl, 4-[2,1,3]benzothiadiazolyl, 2-(4,5,6,7-tetrahydrobenzo)thiazolyl, 7-(2,2-dimethyl-2,3-dihydrobenzo)furanyl, and phenyl. More preferably, R$_8$ is selected from the group consisting of 2-thiazolyl, 2-benzothiazolyl, 4-[2,1,3]benzothiadiazolyl, and phenyl containing one or more substituents, and more preferably, R$_8$ is 2-benzothiazolyl and phenyl.

R$_9$ is selected from the group consisting of hydrogen and lower-alkyl, preferably, hydrogen and methyl, and more preferably, hydrogen.

R$_8$R$_9$—N— is a radical selected from the group consisting of 1-indolinyl, 1-(3,3-dimethylindolinyl), and 1-(1,2,3,4-tetrahydroquinolinyl), preferably, 1-(3,3-dimethylindolinyl) and 1-indolinyl, and more preferably, 1-indolinyl.

The groups represented by R$_7$ other than R$_8$R$_9$N— may be unsubstituted or substituted with one or more substituents selected from the group consisting of lower-alkyl, lower-alkoxy, di-lower-alkylamino, and aryloxy, and the groups represented by R$_8$ and the radical R$_8$R$_9$N— may have one or more substituents selected from the group consisting of hydroxy, halogen, lower-alkyl, lower-alkoxy, amino, mono- or di-lower-alkylamino, lower-alkyl carbonyl, lower-alkoxy carbonyl, and aryloxy, wherein each aryloxy group may be unsubstituted or substituted with one or more substituents independently selected from the group consisting of lower-alkyl, lower-alkoxy, halogen, and trifluoromethyl. Preferably, the substituent groups on R$_7$ are lower-alkyl and the substituent groups on R$_8$ and the radical R$_8$R$_9$N— are selected from the group consisting of hydroxy, lower-alkyl carbonyl, lower-alkoxy carbonyl, and substituted or unsubstituted aryloxy.

In another embodiment, the invention pertains to novel compounds for treating nausea and vomiting in a mammal mediated through 5-HT$_3$ receptors and/or other mechanisms. These 4,5,6,7-tetrahydroimidazo[4,5-c]pyridinyl-6-carboxylic acid derivatives are represented by the formula:

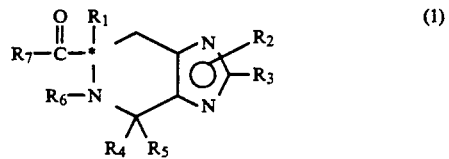

including optically active isomeric forms, and the pharmaceutically acceptable acid addition salts thereof, wherein R$_1$ through R$_9$ are as defined above with the proviso that, when R$_8$ is phenyl, the phenyl group contains at least one substituent independently selected from the group consisting of hydroxy, amino, lower-alkyl carbonyl, lower-alkoxy carbonyl, and aryloxy;

wherein the symbol * represents an asymmetric carbon atom at position 6 which may be in the R or S configuration.

The term "lower-alkyl", as used herein, means branched- or unbranched-hydrocarbon radicals containing from 1 to 6 carbon atoms, preferably from 1 to 3 carbon atoms. The term "halogen", as used herein, includes all four halogens with chlorine being preferred. The term "aryl" means aromatic hydrocarbon radicals such as phenyl, naphthyl, and the like.

In a preferred embodiment, the compounds of the present invention are selected from the group consisting of (R)-6-(2-benzothiazolylaminocarbonyl)-5-methyl-4,5,6,7-tetrahydroimidazo[4,5-c]pyridine, (S)-6-(2- hydroxyphenylaminocarbonyl)-5-methyl-4,5,6,7-tetrahydroimidazo[4,5-c]pyridine, (S)-6-(2-acetylphenylaminocarbonyl)-5-methyl-4,5,6,7-tetrahydroimidazo[4,5-c]pyridine, (S)-6-(2-methoxyphenylaminocarbonyl)-4,4-dimethyl-4,5,6,7-tetrahydroimidazo[4,5-c]pyridine, (S)-6-(2-phenoxyphenylaminocarbonyl)-4,5,6,7-tetrahydroimidazo[4,5-c]pyridine, (S)-6-(2-phenoxy-phenylaminocarbonyl)-4,4-dimethyl-4,5,6,7-tetrahydroimidazo[4,5-c]pyridine, and their pharmaceutically acceptable addition salts. In a more preferred embodiment, the compounds of the present invention are selected from the group consisting of (R)-6-(2-benzothiazolyl)aminocarbonyl-5-methyl-4,5,6,7-tetrahydroimidazo[4,5-c]pyridine, (S)-6-(2-acetylphenyl)aminocarbonyl-5-methyl-4,5,6,7-tetrahydroimidazo[4,5-c]pyridine, (S)-6-(2-phenoxy-phenyl)aminocarbonyl-5-methyl-4,5,6,7-tetrahydroimidazo[4,5-c]pyridine, and their pharmaceutically acceptable addition salts.

fined above. Starting material histidine derivatives of type (2), such as L-histidine, D-histidine, D,L-histidine, 1-methyl-L-histidine, 3-methyl-L-histidine, and alpha-methyl-D,L-histidine, are available commercially from Sigma Chemical Company, St. Louis, Mo. $R_3$ in histidine derivative (2) may be hydrogen. $R_4$ and $R_5$ in the carbonyl compound may be the same or different and may be hydrogen, lower-alkyl, aryl, or aryl lower-alkyl, or $R_4$ and $R_5$ together with the carbon atom to which they are attached form a 5- or 6-member saturated hydrocarbon ring. The starting material histidine derivative (2) may be the D-enantiomer or the L-enantiomer, or may be a mixture of both enantiomers. A D-histidine derivative (2) yields an intermediate (3) with the R configuration and an L-histidine derivative yields an intermediate with the S configuration. Reaction of D-histidine (2) with formaldehyde (HCHO), for example, yields the intermediate, (R)-4,5,6,7-tetrahydroimidazo[4,5-c]pyridinyl-6-carboxylic acid (3).

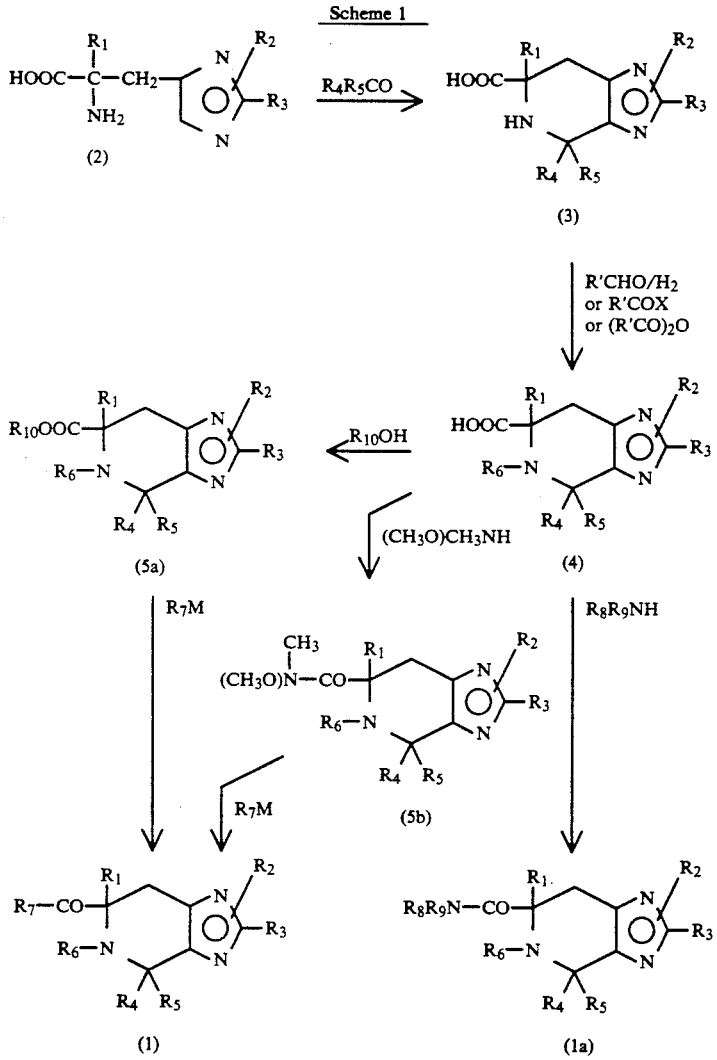

The compounds of the present invention can be prepared by various methods. In one method set out in Scheme 1, a histidine derivative of type (2) is reacted with a carbonyl compound having the formula $R_4R_5CO$ to form an intermediate (3) according to the cyclization procedure of Guzman et al., *J. Med. Chem.*, 27, 564 (1984). $R_1$ and $R_2$ in histidine derivative (2) are as de- Intermediate (3) may then be optionally reductively alkylated at the nitrogen atom at position 5 with an aldehyde compound of type R'CHO in the presence of hydrogen and a catalyst, wherein R' is hydrogen, lower-alkyl, aryl, or aryl lower-alkyl, and R'CH$_2$— equals $R_6$ as defined above, to prepare 5-lower-alkyl or aryl lower-alkyl intermediate (4). Alternatively, intermediate (3) may be optionally acylated at the nitrogen atom at position 5 with a compound of type R'COX or (R'CO)$_2$O, wherein R' is as defined above and X is a halogen, to prepare 5-acyl (formyl, lower-alkyl carbonyl, and arylcarbonyl) intermediate (4) essentially according to the method of Klutchko et al., J. Heterocyclic Chem., 28, 97 (1991). Reaction of 4,5,6,7-tetrahydroimidazo[4,5-c]pyridinyl-6-carboxylic acid (3) with formaldehyde followed by catalytic hydrogenation, for example, yields the 5-methyl intermediate, 5-methyl-4,5,6,7-tetrahydroimidazo[4,5-c]pyridinyl-6-carboxylic acid (4). Reaction of 4,5,6,7-tetrahydroimidazo[4,5-c]pyridinyl-6-carboxylic acid (3) with acetyl chloride yields the 5-acyl spinacine intermediate, 5-acetyl-4,5,6,7-tetrahydroimidazo[4,5-c]pyridinyl-6-carboxylic acid (4).

5-Lower-alkyl or acyl intermediate (4) or intermediate (3) can then be converted into a 6-carboxamide-4,5,6,7-tetrahydroimidazo[4,5-c]pyridine derivative of the present invention having formula (1) by reaction with an amine selected from the group consisting of $R_8R_9$—NH, indoline, 3,3-dimethylindoline, and 1,2,3,4-tetrahydroquinoline, and in the presence of a coupling agent such as a carbodiimide, wherein $R_8$ and $R_9$ are as defined above. Reaction of 5-methyl-4,5,6,7-tetrahydroimidazo[4,5-c]pyridinyl-6-carboxylic acid (4) with 2-hydroxyaniline, for example, yields 6-(2-hydroxyphenylaminocarbonyl)-5-methyl-4,5,6,7-tetrahydroimidazo-[4,5-c]pyridine (1).

Intermediate (3) or 5-lower-alkyl or acyl intermediate (4) may also be converted into a 4,5,6,7-tetrahydroimidazo[4,5-c]pyridine-6-carboxylic acid ester of type (5a) by acid-catalyzed reaction of (3) or (4) with an alcohol represented by the formula $R_{10}OH$, wherein $R_{10}$ is lower-alkyl. Alternatively, intermediate (4) may also be converted to an amide of type (5b) by coupling (3) or (4) with an amine in the presence of a coupling agent such as a carbodiimide. Reaction of 5-methyl-4,5,6,7-tetrahydroimidazo[4,5-c]pyridine-6-carboxylic acid with (methoxy)methylamine in the presence of 1-(3-dimethylaminopropyl)-3-ethylcarbodiimide (EDC) yields the amide (5b). Intermediate (5a or 5b) may in turn be converted into a ketone of type (1) by treatment with a reagent of type $R_7M$ wherein M is lithium or MgBr, such as phenyllithium. Reaction of 5-methyl-4,5,6,7-tetrahydroimidazo[4,5-c]pyridinyl-6-carboxylic acid methyl ester (5a) or N-methoxy N-methyl amide (5b) with phenyllithium, for example, yields 6-benzoyl-5-methyl-4,5,6,7-tetrahydroimidazo[4,5-c]pyridine (1).

Several convenient routes exist for introducing functionalized $R_3$ groups (lower-alkyl, nitro, amino, cyano, and alkylmercapto) in the compounds of formula (1) employing known reaction steps. In one method set out in Scheme 2, the desired compounds having formula (1) can be prepared by reacting intermediate (4') with a nitrating agent, such as HNO$_3$—H$_2$SO$_4$, to form the 2-nitro intermediate (4"). The 2-nitro derivative (4") may then be treated with an amine of type $R_8R_9NH$ to form 2-nitro amide (1'). 2-Nitro amide (1') may then be reduced to form 2-amino amide (1").

Scheme 2

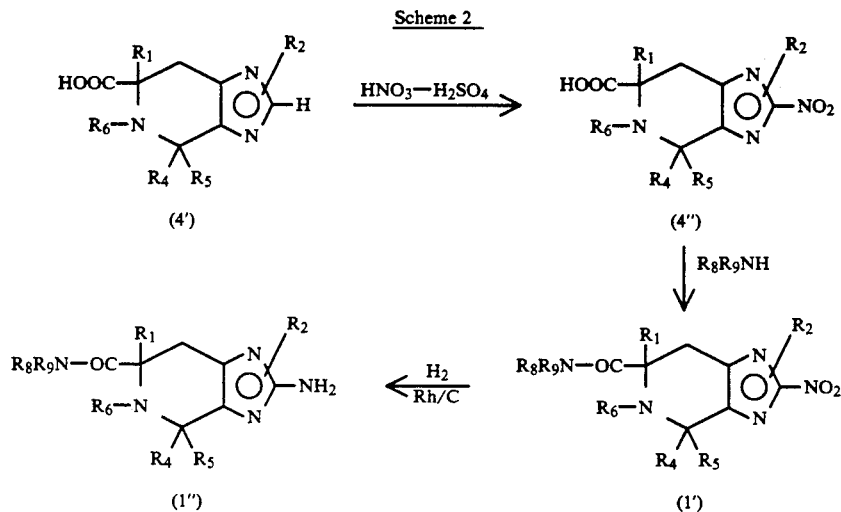

In another method set out in Scheme 3, the desired compounds having formula (1) can be prepared by alkylating intermediate (4') with an alkylating agent, such as methyl iodide (CH$_3$I), in the presence of a strong base, such as lithium diisopropyl amide (LDA), to form the 2-alkyl intermediate (4''').

Scheme 3

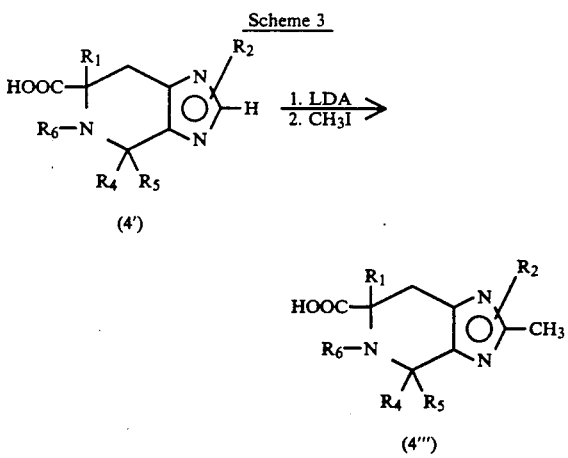

In yet another method set out in Scheme 4, the desired compounds having formula (1) can be prepared by reacting intermediate (4') with a halogenating agent, such as bromine, Br$_2$, to form the 2-bromo intermediate (4$^{iv}$). The 2-bromo derivative (4$^{iv}$) may then be treated with an anion, such as sodium cyanide or a sodium alkyl mercaptan, to form the 2-substituted intermediate (4ᵛ).

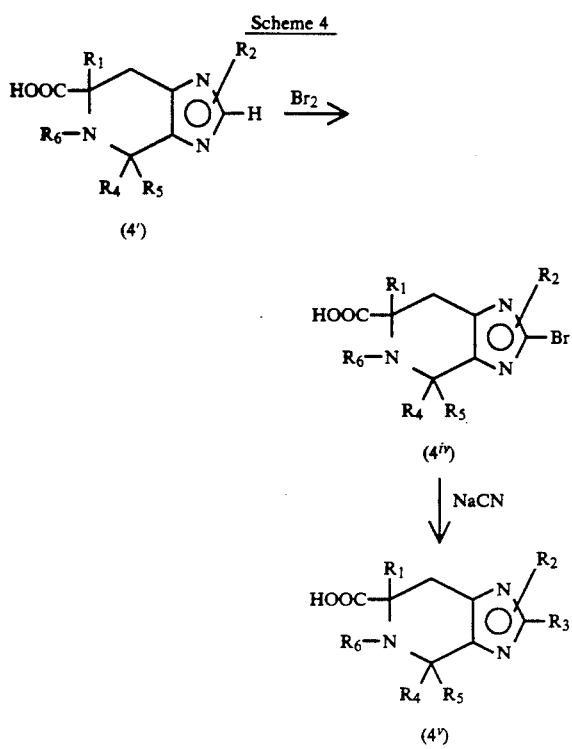

(4')

(4ⁱᵛ)

(4ᵛ)

In a preferred embodiment, the compounds of formula (I) are prepared by a method which comprises the steps of:

(a) reacting a histidine compound having the formula:

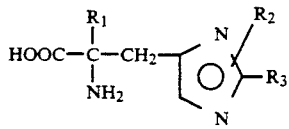

with a carbonyl compound having the formula $R_4R_5CO$ to form a compound (3); wherein $R_1$ through $R_5$ are as defined above; and (b) reacting compound (3) with an amine having the formula $R_8R_9NH$, wherein $R_8$ and $R_9$ are as defined above.

In another embodiment, the method further comprises the step of, prior to step (b), reductively reacting the compound (3) from step (a) with a compound having the formula R'CHO, wherein R' is as defined above, to form a 5-alkyl or 5-arylalkyl intermediate (5).

In yet another embodiment, the method further comprises the step of, prior to step (b), reacting the compound (3) from step (a) with a compound having the formula R'COX or (R'CO)₂O to prepare a 5-acyl intermediate (4), wherein R' is as defined above and X is a halogen.

The compounds of the present invention while effective in the form of the free base may be formulated and administered in the form of pharmaceutically acceptable acid addition salts for purposes of stability, convenience of crystallization, increased solubility and the like. These acid addition salts are formed by conventional methods and include inorganic acid salts such as the hydrochloride, hydrobromide, sulfate, phosphate, and the like; and organic acid salts such as acetate, propionate, benzoate, methanesulfonate, ethanesulfonate, benzenesulfonate, toluenesulfonate, tartrate, citrate, maleate, fumarate, oxalate, and the like. The preferred acid addition salts are the hydrochloride, methanesulfonate, p-toluenesulfonate, and the citrate.

The compounds of the present invention can be combined with a pharmaceutically acceptable carrier to provide a pharmaceutical composition. Suitable carriers for the subject compounds as the free base include propylene glycol-alcohol-water, isotonic water, sterile water for injection (USP), emulphor ™-alcohol-water, cremophor-EL ™ or other suitable carriers known to those skilled in the art.

Suitable carriers for the acid addition salts of the subject compounds include isotonic water, sterile water for injection (USP), alone or in combination with other solubilizing agents such as ethanol, propylene glycol, or other conventional solubilizing agents known to those skilled in the art. A preferred carrier is an isotonic aqueous solution of the inventive compound.

The compounds of the present invention can be administered to mammals, e.g., animals or humans, in amounts effective to provide the desired serotonin antagonist activity. Since the activity of the compounds and the degree of the desired therapeutic effect vary, the dosage level of the compound employed will also vary. The actual dosage administered will also be determined by such generally recognized factors as the body weight of the patient and the individual hypersensitiveness of the particular patient. Thus, the unit dosage for a particular patient (man) can vary from as low as about 0.001 mg per kg of body weight, which the practitioner may titrate to the desired effect. A preferred minimum dose for titration is 0.01 mg/kg body weight.

The compounds of the present invention can be administered by recognized parenteral routes, in the form of sterile solutions or suspensions, in the carriers previously described. These preparations should contain at least about 0.1%, by weight, of the inventive compound but this amount may be varied to between about 0.1% and about 50%, by weight, of the inventive compound. The compounds of the present invention are preferably administered intravenously and the dosage used will generally be in the range from about 0.001 mg to about 500 mg, and preferably from about 0.01 mg to about 50 mg, per 70 kg body weight. This dosage may be administered from 1 to 4 times daily.

The sterile solutions or suspensions may also include the following adjuvants: a sterile diluent, such as water for injection, saline solution, fixed oils, polyethylene glycol, glycerine, propylene glycol, or other synthetic solvent; antibacterial agents, such as benzyl alcohol or methyl paraben; antioxidants, such as ascorbic acid or sodium metabisulfite; chelating agents, such as ethylenediaminetetraacetic acid (EDTA); buffers, such as acetates, citrates or phosphates; and agents for the adjustment of tonicity, such as sodium chloride or dextrose. The parenteral preparations may be enclosed in ampules, disposable syringes, or multiple dosage vials made of glass or plastic.

Throughout this application, various publications have been referenced. The disclosures in these publications are incorporated herein by reference in order to more fully describe the state of the art.

The present invention is further illustrated by the following examples which are presented for purposes of demonstrating, but not limiting, the preparation of the compounds and compositions of this invention. In addition to the parameters set out below, the identity of each compound prepared was confirmed by Nuclear Magnetic Resonance, Infrared Spectroscopy, or both.

EXAMPLE 1

This Example illustrates the preparation of the intermediate (R)-4,5,6,7-tetrahydroimidazo[4,5-c]pyridinyl-6-carboxylic acid hydrochloride ((R)-3a), compound 3 in Scheme 1 wherein $R_1$ through $R_5$ are hydrogen.

Formaldehyde (37% aqueous solution, 15.617 g, 193 mmol) was slowly added to a solution of D-histidine hydrochloride monohydrate (25,025 g, 119 mmol) in water (250 ml) and the mixture was heated to reflux for 1 hour. The solvent was evaporated under vacuum and the residue washed with methanol to yield (R)-4,5,6,7-tetrahydroimidazo[4,5-c]pyridinyl-6-carboxylic acid hydrochloride ((R)-3a) as a white solid (23.199 g, 95.4% yield, dried at 60° C. at 1 mm Hg for 18 hours). m.p.: 283° C. (dec.).

Anal. calcd. for $C_7H_9N_3O_2.HCl$: C, 41.29; H, 4.95; N, 20.64. Found: C, 41.34; H, 4.85; N, 20.37.

When the above reaction was carried out using L-histidine hydrochloride monohydrate, (S)-4,5,6,7-tetrahydroimidazo[4,5-c]pyridinyl-6-carboxylic acid hydrochloride ((S)-3a) was obtained. m.p.: 290° C. (dec.) (276° C.; Akabori et al., *Bull. Chem. Soc., Jap.* 31, 784 (1958)).

Anal. calcd. for $C_7H_9N_3O_2.HCl$: C, 41.29; H, 4.95; N, 20.64. Found: C, 41.03; H, 5.07; N, 20.51.

EXAMPLE 2

This Example illustrates the preparation of the intermediate (S)-4,4-dimethyl-4,5,6,7-tetrahydroimidazo[4,5-c]pyridinyl-6-carboxylic acid hydrochloride ((S)-3b), compound 3 in Scheme 1 wherein $R_1$ through $R_3$ are hydrogen and $R_4$ and $R_5$ are methyl.

L-Histidine hydrochloride monohydrate (20 g, 94.5 mmol) was dissolved in water (500 ml) and acetone (100 ml) and the resulting solution was made alkaline (pH 12) by treatment with sodium hydroxide solution (50% w/w) and heated to reflux overnight. The reaction mixture was then passed through a column of AG-1×8 ion exchange resin (300 meq., hydroxide form). After removal of impurities from the column by elution with water, the product was eluted with 1.8% hydrochloric acid. The solvent was evaporated under vacuum and the residue recrystallized from methanol to yield (S)-4,4-dimethyl-4,5,6,7-tetrahydroimidazo[4,5-c]pyridinyl-6-carboxylic acid dihydrochloride ((S)-3b) as a solid (18.4 g, 100% yield). m.p.: 240° C. (dec.).

Anal. calçd. for $C_9H_{13}N_3O_2.HCl.1/4\ H_2O$: C, 39.65; H, 5.73; N, 15.41. Found: C, 39.61; H, 6.07; N, 15.06.

EXAMPLE 3

This Example illustrates the preparation of the intermediate (R)-5-methyl-4,5,6,7-tetrahydroimidazo[4,5-c]pyridinyl-6-carboxylic acid hydrochloride ((R)-4a), compound 4 in Scheme 1 wherein $R_1$ through $R_5$ are hydrogen and $R_6$ is methyl.

Palladium hydroxide (Pd content 20%, 0.7 g) was added to a solution of compound (R)-3a from Example 1 (16.5 g, 81.1 mmol) and formaldehyde (37% aqueous solution, 8.9 g, 110 mmol) in water (100 ml). The mixture was then hydrogenated on a Parr apparatus (51 psi) at room temperature overnight. After removal of the catalyst by filtration, the filtrate was concentrated under vacuum to yield a foaming solid (19.8 g). The foaming solid (15.1 g) was dissolved in water (30 ml) and passed through a column of AG-50W-X8 ion exchange resin (344 meq, hydrogen form). After removal of impurities from the column by elution with water, the product was eluted with 1.5% ammonium hydroxide solution. After removal of the solvent under vacuum, the residue was triturated with 1,4-dioxane to yield (R)-5-methyl-4,5,6,7-tetrahydroimidazo[4,5-c]pyridinyl-6-carboxylic acid ((R)-4a) as a solid (11.1 g, 91% yield). m.p.: 263°-265° C.

Anal. calcd. for $C_8H_{11}N_3O_2$: C, 53.03; H, 6.12; N, 23.19. Found: C, 52.93; H, 6.09; N, 23.25.

When the above reaction was carried out using (S)-spinacine from Example 1, (S)-5-methyl-4,5,6,7-tetrahydroimidazo[4,5-c]pyridinyl-6-carboxylic acid hydrochloride ((S)-4a) was obtained, m.p.: 262°-263° C.

Anal. calcd. for $C_8H_{11}N_3O_2$: C, 53.03; H, 6.12; N, 23.19. Found: C, 53.09; H, 6.00; N, 23.00.

EXAMPLE 4

This Example illustrates the preparation of the intermediate (S)-4,4-dimethyl-5-methyl-4,5,6,7-tetrahydroimidazo[4,5-c]pyridinyl-6-carboxylic acid dihydrochloride ((S)-4b), compound 4 in Scheme 1 wherein $R_1$ through $R_3$ are hydrogen and $R_4$ through $R_6$ are methyl.

Palladium hydroxide (Pd content 20%, 3.5 g) was added to a solution of (S)-3b from Example 2 (15 g, 76.8 mmol) and formaldehyde (37% aqueous solution, 10 g, 123 mmol) in water (80 ml). The mixture was then hydrogenated on a Parr apparatus (51 psi) at room temperature overnight. After removal of the catalyst by filtration, the filtrate was concentrated under vacuum to yield a foaming solid which was slurried in water (30 ml) and passed through a column of AG-50W-X8 ion exchange resin (300 meq, hydrogen form). After removal of impurities from the column by elution with water, the product was eluted with 1.5% ammonium hydroxide solution. After removal of the solvent under vacuum, the residue was acidified with hydrochloric acid and recrystallized from methanol to yield (S)-4,4-dimethyl-5-methyl-4,5,6,7-tetrahydroimidazo[4,5-c]pyridinyl-6-carboxylic acid dihydrochloride ((S)-4b) as a solid (15.2 g, 94.5% yield). m.p.: 210° C. (dec.).

Anal. calcd. for $C_{10}H_{15}N_3O_2.2HCl.CH_3OH$: C, 42.05; H, 6.74; N, 13.37. Found: C, 41.80; H, 6.81; N, 13.37.

EXAMPLE 5

This Example illustrates the preparation of the intermediate (S)-5-ethyl-4,5,6,7-tetrahydroimidazo[4,5-c]pyridinyl-6-carboxylic acid ((S)-4c), compound 4 in Scheme 1 wherein $R_1$ through $R_5$ are hydrogen and $R_6$ is ethyl.

Palladium hydroxide (Pd content 20%, 0.8 g) was added to a solution of (S)-3a from Example 1 (15.5 g, 76 mmol) and acetaldehyde (9.8 g, 220 mmol) in 80 ml of water. The mixture was then hydrogenated on a Parr apparatus (54 psi) at room temperature overnight. After removal of the catalyst by filtration, the filtrate was concentrated under vacuum to yield a foaming solid (19.1 g). The foaming solid (15.0 g) was dissolved in water (25 ml) and passed through a column of AG-50W-X8 ion exchange resin (300 meq, hydrogen form). After removal of impurities from the column by elution with water, the product was eluted with 1.5% ammonium hydroxide solution. After removal of the solvent under vacuum, the residue yielded (S)-5-ethyl-4,5,6,7-tetrahydroimidazo[4,5-c]pyridinyl-6-carboxylic acid ((S)-4c) as a solid (10.2 g, 73.9% yield). m.p.: 185° C. (dec.)

Anal. calcd. for $C_9H_{13}N_3O_2$: MW 195.22; MS m/z=195[M+].

EXAMPLE 6

This Example illustrates a general method for the preparation of 4,5,6,7-tetrahydroimidazo[4,5-c]pyridinyl-6-carboxamide derivatives according to the present invention.

Compound 3 (Scheme 1) (5 mmol) or a substituted derivative (4) was dissolved in water (5 ml) and hydrochloric acid (5 ml, 1N) and cooled to 0° C. A water-soluble carbodiimide, such as 1-(3-dimethylaminopropyl)-3-ethylcarbodiimide (5.6 mmol), was added to the solution in portions with stirring. After the mixture was stirred at 0° C. for 15 minutes, the desired amine (6 mmol) in dimethylformamide (5 ml), or water (5 ml) if necessary for solubility, was added to the solution. The reaction mixture was then allowed to warm to room temperature and was stirred for two days. The reaction mixture was made alkaline (pH 8) with sodium hydroxide solution (50% w/w) and the solvent was removed under vacuum. The residue was chromatographed on a silica gel column using 8-15% methanol in methylene chloride. After removing the solvent under vacuum, the free base amide was converted to the dihydrochloride in methanol using hydrogen chloride in ethyl ether to yield the desired amide dihydrochloride (1).

EXAMPLE 7

This Example illustrates the preparation of (S)-5-methyl-6-(2-phenoxyphenylaminocarbonyl)-4,5,6,7-tetrahydroimidazo[4,5-c]pyridine dihydrochloride.

To a stirred suspension of (S)-5-methyl-4,5,6,7-tetrahydroimidazo[4,5-c]pyridine monohydrochloride (3.39 g, 15.6 mmol) in 6.8 ml of dimethylformamide, 1-(3-dimethylaminopropyl)-3-ethylcarbodiimide hydrochloride (2.99 g, 15.6 mmol) was added portionwise over 25 minutes at ice bath temperature. The ice bath was removed and a solution of 2-phenoxyaniline (2.89 g, 15.6 mmol) in 10.3 ml of dimethylformamide was added dropwise. After being stirred for 40 hours, the reaction mixture was diluted with water and extracted with methylene chloride. The methylene chloride layer was dried over sodium sulfate ($Na_2SO_4$) and the solvent was removed in vacuo. The residue was chromatographed over silica gel and eluted successively with methylene chloride, methylene chloride:methanol (98:2) and methylene chloride:methanol (95:5) to yield 1.02 g (20%) of the free base. The dihydrochloride salt was recrystallized from 2-propanol, m.p.: 205°-208° C.; $[\alpha]_D = -27.9°$ at 25° C. in methanol (c=0.85).

Anal. calcd. for $C_{20}H_{20}N_4O_2.2HCl$: C, 57.01; H, 5.26; N, 13.30. Found: C, 57.05; H, 5.43; N, 13.17.

EXAMPLE 8

This Example illustrates the preparation of (S)-6-(2,5-dimethoxyphenylaminocarbonyl)-5-methyl-4,5,6,7-tetrahydoimidazo[4,5-c]pyridine dihydrochloride.

(S)-6-(2,5-Dimethoxyphenylaminocarbonyl)-5-methyl-4,5,6,7-tetrahydoimidazo[4,5-c]pyridine dihydrochloride was prepared in 50% yield by the procedure set out above. Physical properties of the dihydrochloride salt: m.p.: 160° C. (dec.); $[\alpha]_D = -50.9°$ C. in methanol (c=1.0).

Anal. calcd. for $C_{16}H_{20}N_4O_3.2HCl.H_2O$: C, 47.18; H, 5.94; N, 13.76. Found: C, 47.49; H, 5.88; N, 13.81.

EXAMPLE 9

This Example illustrates the preparation of (S)-6-(2,5-dihydroxyphenylaminocarbonyl)-5-methyl-4,5,6,7-tetrahydroimidazo[4,5-c]pyridine dihydrobromide.

To a stirred slurry of the above 2,5-dimethoxy compound (free base) (1.0 g, 3.2 mmol) in 20 ml of methylene chloride, $BBr_3$ (22 ml of 1M solution in methylene chloride, 22.0 mmol) was added at −78° C. The reaction mixture was gradually brought to room temperature and stirred for 48 hours. The excess $BBr_3$ was decomposed by dropwise addition of methanol at −20° C. and the contents were evaporated to dryness. The dihydrobromide salt was purified by reprecipitation from methanol-ether. Yield 1.1 g (76%), m.p.: 192° C.

Anal. calcd. for $C_{14}H_{16}N_4O_3.2HBr$: C, 37.36; H, 4.03; N, 12.45. Found: C, 37.41; H, 4.32; N, 12.19.

EXAMPLE 10

This Example illustrates the preparation of (S)-5-acetyl-6-(2-methoxyphenylaminocarbonyl)-4,5,6,7-tetrahydroimidazo[4,5-c]pyridine hydrochloric acid.

Sodium hydride (80% dispersion in mineral oil, 0.55 g, 18 mmol) was added to a solution of (S)-6-(2-methoxyphenyl)aminocarbonyl-4,5,6,7-tetrahydroimidazo[4,5-c]pyridine (2.00 g, 7 mmol) in anhydrous N,N-dimethylformamide (70 ml). The reaction mixture was heated to 80° C. for 30 minutes, then allowed to cool to room temperature. Acetyl chloride (1.46 g, 18 mmol) was added to the reaction mixture at 0° C. The reaction mixture was allowed to warm to room temperature, stirred overnight, and brought to pH 8. Water and N,N-dimethylformamide was distilled off under vacuum. The residue was chromatographed on silica gel with a solvent system of ammonium hydroxide/methanol/methylene chloride (1/8/92 v/v) to yield (S)-5-acetyl-6-(2-methoxyphenylaminocarbonyl)-4,5,6,7-tetrahydroimidazo[4,5-c]pyridine (free base) (1.13 g, 49%). The free base was converted to the hydrochloric acid salt: m.p.: 159° C.

Anal. calcd. for $C_{16}H_{18}N_4O_3.HCl.H_2O$: C, 52.11; H, 5.74; N, 15.19. Found: C, 52.04; H, 5.63; N, 15.03.

EXAMPLE 11

This Example illustrates the preparation of an ester, (S)-5-methyl-4,5,6,7-tetrahydroimidazo[4,5-c]pyridinyl-6-carboxylic acid ethyl ester ((S)-5a), compound 5a in Scheme 1 wherein $R_1$ through $R_5$ are hydrogen, $R_6$ is methyl, and $R_{10}$ is ethyl.

Compound 4a from Example 3 (20 g, 91.9 mmol) was dissolved in absolute ethanol (600 ml) and concentrated sulfuric acid (10 ml) and heated to reflux under a Dean-Stark trap for 24 hours. The solvent was evaporated under vacuum and the residue was neutralized (pH 7) with 1N sodium carbonate solution. The aqueous solution was extracted with methylene chloride (5×160 ml) and the combined organic extracts concentrated. The crude residue was chromatographed on a silica gel column eluting with 10% methanol in methylene chloride to yield (S)-5-methyl-4,5,6,7-tetrahydroimidazo[4,5-c]pyridinyl-6-carboxylic acid ethyl ester ((S)-5a) as a solid (12.7 g, 66.1% yield). m.p.: 72° C.

Anal. calcd. for $C_{10}H_{15}N_3O_2.0.6\ H_2O$: C, 54.58; H, 7.42; N, 19.10. Found: C, 54.62; H, 7.29; N, 19.32.

When the above reaction was carried out using compound 4a from Example 3 and methanol instead of ethanol, (R)-5-methyl-4,5,6,7-tetrahydroimidazo[4,5-c]pyridinyl-6-carboxylic acid methyl ester ((R)-5b) was obtained, compound 5 in Scheme 1 wherein $R_1$ through $R_5$ are hydrogen and $R_6$ and $R_{10}$ are methyl.

Anal. calcd. for $C_9H_{13}N_3O_2$: C, 55.37; H, 6.71; N, 21.52. Found: C, 55.36; H, 6.98; N, 21.19.

EXAMPLE 12

This Example illustrates the preparation of a representative example of ketone compound 1 in Scheme 1, (R)-6-benzoyl-5-methyl-4,5,6,7-tetrahydroimidazo[4,5-c]pyridine oxalic acid).

Phenyllithium (2M cyclohexane/diethyl ether solution (70:30), 6 ml, 12 mmol) was added to a solution of (R)-5-methyl-4,5,6,7-tetrahydroimidazo[4,5-c]pyridinyl-6-carboxylic acid methyl ester from Example 11 (5b, 1.27 g, 6.07 mmol) in dry tetrahydrofuran (50 ml) at $-78°$ C. The reaction mixture was maintained at $-78°$ C. for 15 minutes, then allowed to warm to room temperature. Ethyl acetate (2 ml) was added to the reaction mixture and the solvents were removed under vacuum. The residue was mixed with water (25 ml) and then extracted with methylene chloride. The combined extracts were dried over anhydrous sodium sulfate and evaporated under vacuum. The crude residue (2.38 g) was chromatographed on an alumina column eluting with 3% methanol in methylene chloride to yield (R)-6-benzoyl-5-methyl-4,5,6,7-tetrahydroimidazo[4,5-c]pyridine as a solid (0.406 g, 35% yield). The free base was recrystallized from methanol/ethyl acetate/methyl t-butyl ether. A portion (0.377 g, 1.56 mmol) of the recrystallized free base was converted to its oxalic acid salt (0.436 g, 100% based on oxalic acid used). m.p.: 98° C.

Anal. calcd. for $C_{14}H_{15}N_3O$: C, 58.00; H, 5.17; N, 12.68. Found: C, 58.29; H, 5.41; N, 12.58.

EXAMPLE 13

This Example illustrates the preparation of 6-(N-methoxy-N-methylaminocarbonyl-4,5,6,7)-tetrahydroimidazo[4,5-c]pyridine (5b).

To a solution of (S)-5-methyl-4,5,6,7-tetrahydroimidazo[4,5-c]pyridine-6-carboxylic acid (5.0 g, 27.6 mmol) in water (50 ml) was added O,N-dimethylhydroxylamine hydrochloride (2.83 g, 28.98 mmol) followed by 1-(3-dimethylaminopropyl)-3-ethylcarbodiimide hydrochloride (5.33 g, 27.88 mmol). The reaction mixture was stirred at room temperature for 2 days. The pH of the reaction mixture was adjusted to approximately 8 by addition of 10% sodium carbonate solution and the solvents were removed under reduced pressure. The residual semisolid was triturated with methanol and filtered. The methanol filtrate was evaporated under reduced pressure and the residual material was purified on a silica gel column by elution with 5% methanol in methylene chloride followed by 10% methanol in methylene chloride both containing 0.5% ammonium hydroxide. The desired amide 5b was obtained (4.15 g, 67.1% yield) as white crystals. m.p.: 128°-129° C.;

Anal. calcd. for $C_{10}H_{16}N_4O_2$: C, 53.56; H, 7.19; N, 24.98. Found: C, 53.23; H, 7.15; N, 25.12.

EXAMPLE 14

This Example illustrates the preparation of 6-(2-benzo[b]thiophenylcarbonyl)-5-methyl-4,5,6,7-tetrahydroimidazo[4,5-c]pyridine.

To a flame dried three-neck round bottom flask containing thianaphthene (3.84 g, 28.62 mmol) in anhydrous ether (50 ml) under nitrogen, cooled by an ice bath, was added by syringe, a solution of 1.6M n-butyllithium in hexanes (20 ml, 32 mmol). The mixture was stirred at room temperature for 1 hour and then cooled (ice bath). Compound 5b described above (2.57 g, 11.45 mmol) dissolved in anhydrous tetrahydrofuran (130 ml) was added by syringe. The reaction mixture was stirred at ice bath temperature for 3 hours. The pH of the reaction mixture was made acidic by addition of 5% hydrochloric acid in ethanol and the mixture was concentrated under reduced pressure. The residual material was diluted with water and extracted with methylene chloride. The pH of the aqueous portion was adjusted to about 7-8 by addition of sodium bicarbonate. Attempted partition of the product into ethyl acetate resulted in precipitation of fine off-white solids. The solids were filtered and dried under vacuum (2.34 g, 69% yield). m.p.: 180°-183° C.

The material described above (2.0 g) was dissolved in methanol and filtered. To this solution was added 1M hydrochloric acid solution in ether (17 ml). The solution was mixed well, evaporated under reduced pressure, and the solids recrystallized from methanol-ether. The slightly off-white crystals obtained were dried under vacuum at 60° C. overnight (1.84 g). m.p.: 233°-235° C.

Anal. calcd. for $C_{16}H_{15}N_3OS.2HCl$: C, 51.90; H, 4.63; N, 11.35. Found: C, 51.60; H, 4.61; N, 11.18.

EXAMPLE 15

This Example illustrates the preparation of 6-(2-benzo[b]furanylcarbonyl)-5-methyl-4,5,6,7-tetrahydroimidazo[4,5-c]pyridine.

To a solution of 2,3-benzofuran (2.0 ml, 18.15 mmol, in 50 ml of anhydrous ether) was added 1.6M n-butyllithium in hexanes (12.5 ml, 20 mmol). To the 2-benzofuranyl lithium formed by stirring the solution at room temp. for 1 hour was added (ice bath) the compound 5(b) (1.62 g, 7.22 mmol) dissolved in anhydrous tetrahydrofuran (70 ml). The reaction was continued at ice-bath temperature for 3 hours then worked-up as described to afford 0.89 g (44%) of product as off-white solids. This material was converted to the dihydrochloride by addition of 1M hydrochloric acid in ether (8 ml) as described. The dihydrochloride obtained was recrystallized from methanol-ether and dried under vacuum at 60° C. overnight to afford the ketone dihydrochloride as off-white crystals (0.82 g). m.p.: 193°-195° C.

Anal. calcd. for $C_{16}H_{15}N_3O_2.2HCl.1/2H_2O$: C, 52.90; H, 4.99; N, 11.57. Found: C, 52.52; H, 5.01; N, 11.28.

EXAMPLES 16-64

Further examples of 4,5,6,7-tetrahydroimidazo[4,5-c]pyridinyl-6-carboxamides and ketones within the scope of the present invention which were prepared by procedures analogous to those described above include those set out below in Table 1.

TABLE 1

Chemical Data of 4,5,6,7-Tetrahydroimidazo[4,5-c]pyridinyl-6-carboxylic acid Derivatives

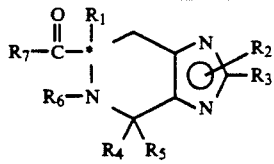

| Compd | *$C_6$ Config. | $R_1$ | $R_2$ | $R_3$ | $R_4$ | $R_5$ | $R_6$ | $R_7$ | % Yield | m.p. °C. (dec.) | Formula |
|---|---|---|---|---|---|---|---|---|---|---|---|
| 1 | R | H | H | H | H | H | $CH_3$ | 2-HO—$C_6H_4$NH— | 37 | 188 | $C_{14}H_{16}N_4O_2.2HCl.0.5H_2O$ |
| 2 | R | H | H | H | H | H | $CH_3$ | 5-Cl-2-$CH_3$O—$C_6H_3$NH— | 49 | 188 | $C_{15}H_{17}N_4O_2Cl.2HCl.0.5H_2O$ |
| 3 | R | H | H | H | H | H | $CH_3$ | 2-$CH_3$O—$C_6H_4$NH— | 65 | 180 | $C_{15}H_{18}N_4O_2.2HCl$ |
| 4 | R | H | H | H | H | H | $CH_3$ | 2-COO$CH_3$—$C_6H_4$NH— | 17 | 169 | $C_{16}H_{18}N_4O_3.2HCl$ |
| 5 | R | H | H | H | H | H | $CH_3$ | 2-CO$CH_3$—$C_6H_4$NH— | 16 | 180 | $C_{16}H_{18}N_4O_2.2HCl.0.25H_2O$ |
| 6 | S | H | H | H | H | H | $CH_3$ | 2-$CH_3$O—$C_6H_4$NH— | 96 | 178 | $C_{15}H_{18}N_4O_2.2HCl.0.5H_2O$ |
| 7 | S | H | H | H | H | H | $CH_3$ | 5-Cl-2-$CH_3$O—$C_6H_3$NH— | 26 | 185 | $C_{15}H_{17}N_4O_2.2HCl$ |
| 8 | R | H | H | H | H | H | H | 2-$CH_3$O—$C_6H_4$NH— | 49 | 253 | $C_{14}H_{16}N_4O_2.2HCl.0.25H_2O$ |
| 9 | R | H | H | H | H | H | $CH_3$ | $C_6H_5$NH— | 59 | 208 | $C_{14}H_{16}N_4O.2HCl$ |
| 10 | R | H | H | H | H | H | $CH_3$ | 2-$C_2H_5$O—$C_6H_4$NH— | 23 | 187 | $C_{16}H_{20}N_4O_2.2HCl$ |
| 11 | R | H | H | H | H | H | $CH_3$ | 2-$C_6H_5$O—$C_6H_4$NH— | 17 | 192 | $C_{20}H_{20}N_4O_2.2HCl.0.25H_2O$ |
| 12 | R | H | H | H | H | H | $CH_3$ | 2-thiadiazolyl-NH— | 28 | 200 | $C_{11}H_{13}N_5OS.3HCl.0.5H_2O$ |
| 13 | R | H | H | H | H | H | $CH_3$ | 2-benzothiazolyl-NH— | 17 | 215 | $C_{15}H_{15}N_5OS.2HCl$ |
| 14 | S | H | H | H | H | H | H | 2-$CH_3$O—$C_6H_4$NH— | 71 | 243 | $C_{14}H_{16}N_4O_2.2HCl$ |
| 15 | S | H | H | H | H | H | $CH_3$ | 2-HO—$C_6H_4$NH— | 20 | 202 | $C_{14}H_{16}N_4O_2.2HCl$ |
| 16 | S | H | H | H | H | H | $CH_3$ | 2-COO$CH_3$—$C_6H_4$NH— | 15 | 174 | $C_{16}H_{18}N_4O_3.2HCl$ |
| 17 | S | H | H | H | H | H | $CH_3$ | 2-$C_2H_5$O—$C_6H_4$NH— | 9 | 157 | $C_{16}H_{20}N_4O_2.2HCl.0.75H_2O$ |
| 18 | S | H | H | H | H | H | $C_2H_5$ | 2-HO—$C_6H_4$NH— | 25 | 130 | $C_{15}H_{18}N_4O_2.2C_2H_2O_4$ |
| 19 | R | H | H | H | H | H | $CH_3$ | $C_6H_5$— | 35 | 98 | $C_{14}H_{15}N_3O.C_2H_2O_4$ |
| 20 | S | H | H | H | $CH_3$ | $CH_3$ | $CH_3$ | 2-$CH_3$O—$C_6H_4$NH— | 7 | 210 | $C_{16}H_{20}N_4O_2.2HCl.1.0H_2O$ |
| 21 | R | H | H | H | H | H | $CH_3$ | 4-[2,1,3-benzothiadiazol]yl-NH— | 16 | 200 | $C_{14}H_{14}N_6OS.2HCl.0.75H_2O$ |
| 22 | S | H | H | H | H | H | $CH_3$ | 2-benzothiazolyl-NH— | 12 | 213 | $C_{15}H_{15}N_5OS.2HCl.1.25H_2O$ |
| 23 | S | H | H | H | H | H | $CH_3$ | 4-[2,1,3-benzothiadiazol]yl-NH— | 8 | 168 | $C_{14}H_{14}N_6OS.2HCl$ |
| 24 | S | H | H | H | $CH_3$ | $CH_3$ | $CH_3$ | 2-HO—$C_6H_4$NH— | 19 | 205 | $C_{16}H_{20}N_4O_2.2HCl$ |
| 25 | S | H | H | H | $CH_3$ | $CH_3$ | $CH_3$ | 2-$CH_3$O—$C_6H_4$NH— | 24 | 190 | $C_{17}H_{22}N_4O_2.2HCl.0.25H_2O$ |
| 26 | S | H | H | H | H | H | $CH_3$ | 2-$C_6H_5$C(O)NH—$C_6H_4$NH— | 28 | 205 | $C_{21}H_{21}N_5O_2.2HCl$ |
| 27 | S | H | H | H | H | H | $CH_3$ | 2-$C_6H_5$O—$C_6H_4$NH— | 49 | 205–208 | $C_{20}H_{20}N_4O_2.2HCl$ |
| 28 | S | H | H | H | H | H | $CH_3$ | 2-thienyl | 56 | 199–201 | $C_{21}H_{13}N_3OS.2HCl$ |
| 29 | S | H | H | H | H | H | $CH_3$ | 2-F—$C_6H_4$NH— | 47 | 95–97 | $C_{14}H_{15}N_4OF.2HCl$ |
| 30 | S | H | H | H | H | H | $CH_3$ | 2,5-($CH_3$O)$_2C_6H_3$NH— | 53 | 160 | $C_{16}H_{20}N_4O_3.2HCl.1.0H_2O$ |
| 31 | S | H | H | H | H | H | $CH_3$ | 2,3-(F)$_2C_6H_3$NH— | 39 | 150 | $C_{14}H_{14}N_4OF_2.2HCl.1.0H_2O$ |
| 32 | S | H | H | H | H | H | $CH_3$ | 2-benzo[b]thiophenyl | 69 | 233–235 | $C_{16}H_{15}N_3OS.2HCl$ |
| 33 | S | H | H | H | H | H | $CH_3$ | 2-benzo[b]furanyl | 78 | 193–195 | $C_{16}H_{15}N_3O_2.2HCl.0.5H_2O$ |
| 34 | S | H | H | H | H | H | $CH_3$ | 2,6-(F)$_2C_6H_3$NH— | 23 | 125 | $C_{14}H_{14}N_4OF_2.2HCl.1.25H_2O$ |
| 35 | S | H | H | H | H | H | $CH_3$ | 2,3,4-(F)$_3C_6H_2$NH— | 30 | 139 | $C_{14}H_{13}N_4OF_3.2HCl.1.0H_2O$ |
| 36 | S | H | H | H | H | H | $CH_3$ | 8-(1,2,3,4-tetrahydroquinolin)yl-NH— | 29 | 133 | $C_{17}H_{21}N_5O.3HCl.0.5H_2O$ |
| 37 | S | H | H | H | H | H | $CH_3$ | 2-Cl—$C_6H_4$NH— | 18 | 143 | $C_{14}H_{15}N_4OCl.2HCl$ |
| 38 | S | H | H | H | H | H | $CH_3$ | $C_6H_5$— | 38 | 95–98 | $C_{14}H_{15}N_3O.C_2H_2O_4$ |
| 39 | S | H | H | H | H | H | $CH_3$ | 2-$CH_3$C(O)$C_6H_4$NH— | 26 | 191 | $C_{16}H_{18}N_4O_2.2HCl.0.5H_2O$ |
| 40 | S | H | H | H | H | H | $CH_3$ | 2,5-(OH)$_2C_6H_3$NH— | 78 | 192 | $C_{14}H_{16}N_4O_3.2HBr$ |
| 41 | S | H | H | H | H | H | $CH_3$ | 2-(5-($CH_3$O)-benzo[b]furan)yl- | 63 | 214–218 | $C_{17}H_{17}N_3O_3.2HCl.1.0H_2O$ |
| 42 | S | H | H | H | H | H | $CH_3$ | 2-$NH_2$—$C_6H_4$NH— | 13 | 200 | $C_{14}H_{17}N_5O.3HCl.0.5H_2O$ |
| 43 | S | H | H | H | H | H | $CH_3$ | 2-$CH_3$O—$C_6H_4$— | 54 | 221–223 | $C_{15}H_{17}N_3O_2.2HCl$ |
| 44 | S | H | H | H | H | H | $CH_3$ | 2-(3-$CF_3C_6H_4$O—)$C_6H_4$NH— | 54 | 235–237 | $C_{21}H_{19}N_4O_2F_3.2HCl$ |
| 45 | S | H | H | H | H | H | $CH_3$ | 2-(3-$FC_6H_4$O—)$C_6H_4$NH— | 29 | 120 | $C_{20}H_{19}N_4O_2.2HCl$ |
| 46 | S | H | H | H | H | H | $CH_3$ | 2,5-($CH_3$O)$_2C_6H_3$NH— | 84 | 229–231 | $C_{16}H_{20}N_4O_3.2HCl.0.25H_2O$ |
| 47 | S | H | H | H | H | H | $CH_3$CO— | 2-$CH_3$O$C_6H_4$NH— | 49 | 159 | $C_{16}H_{18}N_4O_3.2HCl.1.0H_2O$ |
| 48 | S | H | H | H | $CH_3$ | $CH_3$ | H | 2-$CH_3$CO$C_6H_4$NH— | 22 | 210 | $C_{17}H_{20}N_4O_2.2HCl.0.75H_2O$ |
| 49 | S | H | H | H | $CH_3$ | $CH_3$ | H | 2-$C_6H_5$O$C_6H_4$NH— | 17 | 204 | $C_{21}H_{22}N_4O_2.2HCl.0.5H_2O$ |

EXAMPLE 65

A pharmaceutical composition for antagonism of 5-$HT_3$ receptors can be prepared from the following ingredients:

| COMPONENTS | AMOUNTS |
|---|---|
| (S)-6-(2-hydroxyphenylaminocarbonyl)-5-methyl-4,5,6,7-tetrahydroimidazo[4,5-c]pyridine | 1–30 mg |

| -continued | |
|---|---|
| COMPONENTS | AMOUNTS |
| isotonic water | 1 ml |

Of course, other compounds of this invention such as those set out in Examples 16-64 may be utilized as the active component in the above formulation.

EXAMPLE 66

A number of compounds in accordance with the present invention were tested for their 5-HT$_3$ and D$_2$ binding affinities in accord with the following procedures.

Binding Methodologies for 5-HT$_3$ and D$_2$ Assays

Male Sprague-Dawley rats (175-220 g) were sacrificed by decapitation and their brains removed rapidly. The entorhinal cortex was used for the 5-HT$_3$ (5-hydroxytryptamine) binding assay and the remainder of the brain, minus the brain stem and cerebellum, was used for the D$_2$ (dopamine) binding assay. The entorhinal cortex was harvested and prepared on the day of the assay.

The entorhinal cortex was homogenized in 20 volumes of cold 50 mM HEPES buffer, pH 7.4, while the remaining brain tissue was homogenized in 20 volumes of cold 50 mM Tris, pH 7.4. The homogenates were centrifuged at 4800×g for 15 minutes at 5° C. and the supernatants decanted. Pellets were resuspended in the original volume of HEPES or Tris. Homogenates were centrifuged and the supernatants decanted. Pellets were resuspended in the same volume of HEPES or Tris and incubated at 37° C. for 45 minutes to remove endogenous neurotransmitters. Homogenates were centrifuged and the supernatants were decanted. Pellets for D$_2$ assays were stored at −50° C. until the day of the assay. The pellets for the 5-HT$_3$ assay (entorhinal cortex) were resuspended in the appropriate amount of HEPES buffer and used promptly. Modifications of published assays for [$^3$H]GR65630 (Kilpatrick et al., Nature: 330, 746-748 (1987)) and [$^3$H]raclopride (Dewar et al., J. Pharmacol. Exp. Ther.: 250, 696-706 (1989) and Lidow et al., Proc. Natl. Acad. Sci. USA: 86, 6412-6416 (1989)) were used for the 5-HT$_3$ and D$_2$ binding assays, respectively.

Briefly, 0.25 ml of homogenate was incubated with either 0.2 nM of [$^3$H]GR65630 or 1.0 nM of [$^3$H]raclopride in a final volume of 0.5 ml. D$_2$ binding also requires sodium chloride and potassium chloride (120 mM and 5 mM, final concentration, respectively). In the 5-HT$_3$ assay, non-specific binding was defined in the presence of 100 uM quipazine. In the D$_2$ assay, non-specific binding was defined in the presence of 100 uM of (+/−) sulpiride. Both assays were incubated at room temperature; [$^3$H]GR65630 for 40 minutes and [$^3$H]raclopride for 60 minutes. Test compounds (0.1 ml) were added to incubates where appropriate. Bound ligand was separated from free ligand by filtration and quantified using liquid scintillation spectrophotometry. IC$_{50}$ values were calculate for all test compounds.

Cisplatin Ferret Assay—Antiemetic Screening

Male ferrets (castrated, descented, 1-2 kg) were purchased from Triple F Farms, Syre, Pa. Ferrets were housed four in a cage with a 12 hour light cycle and were fed ad libitum with Ralston Purina Cat Chow. Each ferret was used unfasted for the assay after a minimum of a 24 hour acclimation time in animal facility.

Ferret Preparation. Each ferret was anesthetized with 5% isoflurane-O$_2$ in a 20 gallon aquarium for 2 to 5 minutes. After removal of the anesthetic gas, the animals were removed and weighed. Injections were made into the dorsal front paw vein using a tourniquet and a 1 ml tuberculin syringe with a 25 g needle while the animal was maintained under anesthesia using a small nose cone delivering 5% isoflurane-O$_2$. Cisplatin was injected using a 3 ml or 5 ml syringe in the opposite paw from the study compound or saline. Recovery time from anaesthesia was 5 to 8 minutes.

Drug Preparation. Cisplatin bulk powder was weighed and dissolved in normal saline at 75° C. to provide a 5 mg/ml solution (90 mg was placed in a scintillation vial and qs with 18 ml saline). The solution was stirred and maintained at 40° C. until ready for use. The study drug was weighed and dissolved in normal saline at room temperature to provide a 1 mg/ml solution (10 mg was placed in a scintillation vial and qs with 10 ml saline). Suspensions were heated to 40° C. to bring the study compound into solution. Compounds not soluble under these conditions were not assayed.

Assay. Cisplatin was injected i.v. at 10 mg/kg into twelve anesthetized ferrets daily at time zero. Normal saline (0.5 ml) or the study compound (0.1 or 1.0 mg/kg) was injected 30 minutes later in groups of three anesthetized ferrets. Order of treatment and treatment dose was selected at random, with the remaining treatment dose assayed in the next experiment.

Experimental Observations and Data Collection. Ferrets were viewed individually. The time and number of emetic episodes were recorded for four hours. Zero time was equivalent to the time of cisplatin injection. An episode was defined as an expulsion of solids or liquid, or a retching which resulted in an open mouth without expulsion. Retches were recorded but not counted. The total number of episodes for each of the four groups of three ferrets (+/−S.E.) was averaged and the effect of treatment (% protection) was calculated as the percent reduction of emetic episodes compared to controls.

$$\text{Percent Protection} = \frac{\text{No. of Episodes (saline)} - \text{No. of Episodes (drug)}}{\text{No. of Episodes (saline)}} \times 100$$

Percent protection values were determined from experimental controls. Experimental controls were those obtained from the day of the experiment. Onset times of the first episode were averaged and recorded for each group. Prodromal signs (lip licking, slit eyes, head shaking, salivation, scratching, clawing, walking backward, sedation, urination, and defecation) were also averaged and recorded.

The compounds listed in Table 2 were tested by these procedures and found to have the activities listed in the columns on the right side of Table 2. In Table 2, 5-HT$_3$, IC$_{50}$, nM means the concentration of test compound that displaces 50% of the radiolabelled ligand; ED$_{50}$, mg/kg means the median effective dose in terms of milligram per kilogram of body weight, a dose that produces its effect in 50% of the population; % Prot, 0.1 mg/kg means the effect of treatment of 0.1 mg/kg dose of drug. For all the compounds reported in Table 2 set out below, the IC$_{50}$ value for D$_2$ receptor binding was >10,000 nm.

TABLE 2

Pharmacological Data of 4,5,6,7-Tetrahydroimidazo[4,5-c]pyridinyl-6-carboxylic Acid Derivatives

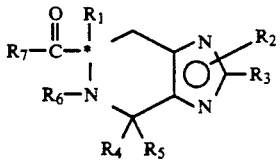

| Compd | *C6 Config. | R1 | R2 | R3 | R4 | R5 | R6 | R7 | 5-HT3 IC50, nM | Ferret Cisplatin Test ED50, mg/Kg | % Prot 0.1 mg/Kg |
|---|---|---|---|---|---|---|---|---|---|---|---|
| 1 | R | H | H | H | H | H | CH3 | 2-HO—C6H4NH— | 10.9 | 0.063 | 73 |
| 2 | R | H | H | H | H | H | CH3 | 5-Cl-2-CH3O—C6H3NH— | 10.02 | 0.4 | 31 |
| 3 | R | H | H | H | H | H | CH3 | 2-CH3O—C6H4NH— | 47.63 | 2.08 | 9 |
| 4 | R | H | H | H | H | H | CH3 | 2-COOCH3—C6H4NH— | 12.13 | 0.1 | 33 |
| 5 | R | H | H | H | H | H | CH3 | 2-COCH3—C6H4NH— | 4.26 | 0.123 | 22 |
| 6 | S | H | H | H | H | H | CH3 | 2-CH3O—C6H4NH— | 4.86 | 0.023 | 77 |
| 7 | S | H | H | H | H | H | CH3 | 5-Cl-2-CH3O—C6H3NH— | 6.26 | 0.14 | 57 |
| 8 | R | H | H | H | H | H | H | 2-CH3O—C6H4NH— | 10.45 | — | 62 |
| 9 | R | H | H | H | H | H | CH3 | C6H5NH— | 57.23 | 0.33 | 26 |
| 10 | R | H | H | H | H | H | CH3 | 2-C2H5O—C6H4NH— | 4.14 | 0.31 | 29 |
| 11 | R | H | H | H | H | H | CH3 | 2-C6H5O—C6H4NH— | 8.19 | 0.47 | 15 |
| 12 | R | H | H | H | H | H | CH3 | 2-thiadizolyl-NH— | 273.46 | | 40 |
| 13 | R | H | H | H | H | H | CH3 | 2-benzothiazolyl-NH— | 71.52 | 0.074 | 76 |
| 14 | S | H | H | H | H | H | H | 2-CH3O—C6H4NH— | 8.53 | 0.062 | 48 |
| 15 | S | H | H | H | H | H | CH3 | 2-HO—C6H4NH— | 62.37 | 0.007 | 99 |
| 16 | S | H | H | H | H | H | CH3 | 2-COOCH3—C6H4NH— | 29.03 | 0.01 | 42 |
| 17 | S | H | H | H | H | H | CH3 | 2-C2H5O—C6H4NH— | 15.37 | 0.2 | 58 |
| 18 | S | H | H | H | H | H | C2H5 | 2-HO—C6H4NH— | 17.6 | 0.16 | 46 |
| 19 | R | H | H | H | H | H | CH3 | C6H5— | 58.51 | — | 8 |
| 20 | S | H | H | H | CH3 | CH3 | CH3 | 2-CH3O—C6H4NH— | 21.69 | 0.008 | 72 |
| 21 | R | H | H | H | H | H | CH3 | 4-[2,1,3-benzothiadiazol]yl-NH— | 1.98 | 0.39 | 24 |
| 22 | S | H | H | H | H | H | CH3 | 2-benzothiazolyl-NH— | 37.18 | — | 14 |
| 23 | S | H | H | H | H | H | CH3 | 4-[2,1,3-benzothiadiazol]yl-NH— | 15.88 | 0.016 | 100 |
| 24 | S | H | H | H | CH3 | CH3 | CH3 | 2-HO—C6H4NH— | 47.2 | 0.025 | 48 |
| 25 | S | H | H | H | CH3 | CH3 | CH3 | 2-CH3O—C6H4NH— | 14.05 | 0.026 | 93 |
| 26 | S | H | H | H | H | H | CH3 | 2-C6H5C(O)NH—C6H4NH— | 289.14 | — | 0 |
| 27 | S | H | H | H | H | H | CH3 | 2-C6H5O—C6H4NH— | 6.92 | 0.031 | 72 |
| 28 | S | H | H | H | H | H | CH3 | 2-thienyl | 647.79 | — | 0 |
| 29 | S | H | H | H | H | H | CH3 | 2-F—C6H4NH— | 335.50 | 0.024 | 88 |
| 30 | S | H | H | H | H | H | CH3 | 2,5-(CH3O)2C6H3NH— | 69.73 | — | 5 |
| 31 | S | H | H | H | H | H | CH3 | 2,3-(F)2C6H3NH— | 643.79 | 0.068 | 91 |
| 32 | S | H | H | H | H | H | CH3 | 2-benzo[b]thiophenyl | 234.48 | 0.11 | 41 |
| 33 | S | H | H | H | H | H | CH3 | 2-benzo[b]furanyl | 2023.94 | 0.43 | 31 |
| 34 | S | H | H | H | H | H | CH3 | 2,6-(F)2C6H3NH— | 611.88 | 0.15 | 59 |
| 35 | S | H | H | H | H | H | CH3 | 2,3,4-(F)3C6H2NH— | 159.88 | 0.19 | 20 |
| 36 | S | H | H | H | H | H | CH3 | 8-(1,2,3,4-tetrahydro-quinolin)yl-NH— | 102.84 | 0.081 | 70 |
| 37 | S | H | H | H | H | H | CH3 | 2-Cl—C6H4NH— | 26.74 | 0.065 | 42 |
| 38 | S | H | H | H | H | H | CH3 | C6H5— | 48.45 | — | 30 |
| 39 | S | H | H | H | H | H | CH3 | 2-CH3C(O)C6H4NH— | 4.18 | 0.045 | 65 |
| 40 | S | H | H | H | H | H | CH3 | 2,5-(OH)2C6H3NH— | 45.92 | — | 0 |
| 41 | S | H | H | H | H | H | CH3 | 2-(5-(CH3O)-benzo[b]furan)yl- | 12881.17 | — | 9 |
| 42 | S | H | H | H | H | H | CH3 | 2-NH2—C6H4NH— | 3494.32 | 0.23 | 39 |
| 43 | S | H | H | H | H | H | CH3 | 2-CH3O—C6H4— | 2377.80 | — | 41 |
| 44 | S | H | H | H | H | H | CH3 | 2-(3-CF3C6H4O—)C6H4NH— | 9.52 | 0.26 | 1 |
| 45 | S | H | H | H | H | H | CH3 | 2-(3-FC6H4O—)C6H4NH— | 7.09 | 0.042 | 67 |
| 46 | S | H | H | H | H | H | CH3 | 2,5-(CH3O)2C6H4NH— | 162.26 | — | 50 |
| 47 | S | H | H | H | H | H | CH3CO | 2-CH3OC6H4NH— | — | 0.044 | 81 |
| 48 | S | H | H | H | CH3 | CH3 | H | 2-CH3COC6H4NH— | 158.21 | 0.0098 | 100 |
| 49 | S | H | H | H | CH3 | CH3 | H | 2-C6H5OC6H4NH— | 8.55 | 0.022 | 76 |
| 50 | Granisetron | | | | | | | | 1.05 | 0.030 | 71 |
| 51 | Metaclopramide | | | | | | | | 514.00 | 4.08 | 17 |
| 52 | Ondansetron | | | | | | | | 5.00 | 0.041 | 77 |

While we have represented a number of embodiments of this invention, it is apparent that the basic construction can be altered to provide other embodiments which utilize the invention without departing from the spirit and scope of the invention. All such modifications and variations are intended to be included within the scope of the invention as defined in the appended claims rather than the specific embodiments which have been presented by way of example.

We claim:

1. A 4,5,6,7-tetrahydroimidazo[4,5-c]pyridinyl-6-carboxylic acid derivative represented by the formula:

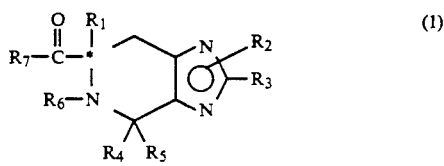

including optically active isomeric forms, and the pharmaceutically acceptable acid addition salts thereof, wherein:

R₁ and R₂ are individually hydrogen or lower-alkyl;

R₃ is selected from the group consisting of hydrogen, lower-alkyl, nitro, amino, cyano, and alkylmercapto;

R₄ and R₅ are independently selected from the group consisting of hydrogen, lower-alkyl, aryl, and aryl lower-alkyl, or R₄ and R₅ together with the carbon atom to which they are attached form a 5- or 6-member saturated hydrocarbon ring;

R₆ is selected from the group consisting of hydrogen, lower-alkyl, aryl lower-alkyl, formyl, lower-alkyl carbonyl, and aryl carbonyl;

R₇ is selected from the group consisting of phenyl, thienyl, indolyl, indazolyl, benzo[b]furanyl, benzo[b]thiophenyl, and R₈R₉—N—; and R₈ is selected from the group consisting of 8-[1,2,3,4-tetrahydroquinolinyl], pyridinyl, 3-quinolinyl, 2-naphthalinyl, 2-thiazolyl, 2-benzothiazolyl, 4-[2,1,3]benzothiadiazolyl, 2-(4,5,6,7-tetrahydrobenzo)thiazolyl, 7-(2,2-dimethyl-2,3-dihydrobenzo)furanyl, and phenyl;

R₉ is hydrogen or lower-alkyl;

R₈R₉—N— is a radical selected from the group consisting of 1-indolinyl, 1-(3,3-dimethylindolinyl), and 1-(1,2,3,4-tetrahydroquinolinyl); wherein the groups represented by R₇ other than R₈R₉N— may be unsubstituted or substituted with one or more substituents selected from the group consisting of lower-alkyl, lower-alkoxy, di-lower-alkylamino, and aryloxy, and the groups represented by R₈ and the radical R₈R₉N— may have one or more substituents selected from the group consisting of hydroxy, halogen, lower-alkyl, lower-alkoxy, amino, mono-or di-lower-alkylamino, lower-alkyl carbonyl, lower-alkoxy carbonyl, and aryloxy, wherein each aryloxy group may be unsubstituted or substituted with one or more substituents independently selected from the group consisting of lower-alkyl, lower-alkoxy, halogen, and trifluoromethyl with the proviso that, when R₈ is phenyl, said phenyl group contains at least one substituent; wherein the symbol * represents an asymmetric carbon atom at position 6 which may be in the R or S configuration, and each lower-alkyl group contains from 1 to 6 carbon atoms.

2. The compound according to claim 1, wherein R₁, R₂, R₄, and R₅ are individually hydrogen or methyl.

3. The compound according to claim 1, wherein R₃ is selected from the group consisting of hydrogen, lower-alkyl, nitro, and amino.

4. The compound according to claim 1, wherein R₁, R₂, and R₃ are hydrogen.

5. The compound according to claim 1, wherein R₆ is hydrogen or lower-alkyl.

6. The compound according to claim 1, which comprises (R)-6-(2-benzothiazolylaminocarbonyl)-5-methyl-4,5,6,7-tetrahydroimidazo[4,5-c]pyridine, and the pharmaceutically acceptable addition salts thereof.

7. The compound according to claim 1, wherein R₇ is R₈R₉—N—, R₈ is phenyl containing one or more substituents independently selected from the group consisting of hydroxy, aryloxy, lower-alkyl carbonyl, and lower-alkoxy carbonyl, and R₉ is hydrogen.

8. The compound according to claim 7, which comprises (S)-6-(2-acetylphenylaminocarbonyl)-5-methyl-4,5,6,7-tetrahydroimidazo[4,5-c]pyridine, and the pharmaceutically acceptable addition salts thereof.

9. The compound according to claim 7, which comprises (S)-6-(2-phenoxyphenylaminocarbonyl)-5-methyl-4,5,6,7-tetrahydroimidazo[4,5-c]pyridine, and the pharmaceutically acceptable addition salts thereof.

10. The compound according to claim 1, wherein R₇ is selected from the group consisting of phenyl, thienyl, indolyl, indazolyl, benzo[b]furanyl, and benzo[b]thiophenyl.

11. A pharmaceutical composition for treating a nausea and vomiting condition in a mammal which comprises a pharmaceutically acceptable carrier and a therapeutically effective amount of a 4,5,6,7-tetrahydroimidazo[4,5-c]pyridinyl-6-carboxylic acid derivative represented by the formula:

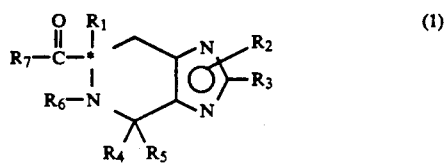

including optically active isomeric forms, and the pharmaceutically acceptable acid addition salts thereof, wherein:

R₁ and R₂ are individually hydrogen or lower-alkyl;

R₃ is selected from the group consisting of hydrogen, lower-alkyl, nitro, amino, cyano, and alkylmercapto;

R₄ and R₅ are independently selected from the group consisting of hydrogen, lower-alkyl, aryl, and aryl lower-alkyl, or R₄ and R₅ together with the carbon atom to which they are attached form a 5- or 6-member saturated hydrocarbon ring;

R₆ is selected from the group consisting of hydrogen, lower-alkyl, aryl lower-alkyl, formyl, lower-alkyl carbonyl, and aryl carbonyl;

R₇ is selected from the group consisting of phenyl, thienyl, indolyl, indazolyl, benzo[b]furanyl, benzo[b]thiophenyl, and R₈R₉—N—; and R₈ is selected from the group consisting of 8-[1,2,3,4-tetrahydroquinolinyl], pyridinyl, 3-quinolinyl, 2-naphthalinyl, 2-thiazolyl, 2-benzothiazolyl, 4-[2,1,3]benzothiadiazolyl, 2-(4,5,6,7-tetrahydrobenzo)thiazolyl, 7-(2,2-dimethyl-2,3-dihydrobenzo)furanyl, and phenyl;

R₉ is hydrogen or lower-alkyl;

R₈R₉—N— is a radical selected from the group consisting of 1-indolinyl, 1-(3,3-dimethylindolinyl), and 1-(1,2,3,4-tetrahydroquinolinyl); wherein the groups represented by R₇ other than R₈R₉N— may be unsubstituted or substituted with one or more substituents selected from the group consisting of lower-alkyl, lower-alkoxy, di-lower-alkylamino, and aryloxy, and the groups represented by R₈ and the radical R₈R₉N— may have one or more substituents selected from the group consisting of hydroxy, halogen, lower-alkyl, lower-alkoxy, amino, mono-or di-lower-alkylamino, lower-alkyl carbonyl, lower-alkoxy carbonyl, and aryloxy, wherein each aryloxy group may be unsubstituted or substituted with one or more substituents independently selected from the group consisting of lower-alkyl, lower-alkoxy, halogen, and trifluoromethyl with the proviso that, when $R_8$ is phenyl, said phenyl group contains at least one substituent; wherein the symbol * represents an asymmetric carbon atom at position 6 which may be in the R or S configuration, and each lower-alkyl group contains from 1 to 6 carbon atoms.

12. A method for treating a condition of nausea and vomiting in a mammal which comprises administering to the mammal an amount, therapeutically effective to relieve the condition, of a 4,5,6,7-tetrahydroimidazo[4,5-c]pyridinyl-6-carboxylic acid derivative represented by the formula:

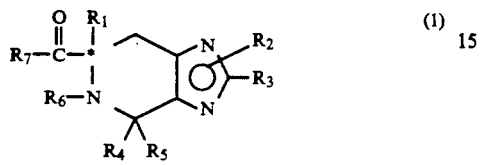

(1)

including optically active isomeric forms, and the pharmaceutically acceptable acid addition salts thereof, wherein:

$R_1$ and $R_2$ are individually hydrogen or lower-alkyl;

$R_3$ is selected from the group consisting of hydrogen, lower-alkyl, nitro, amino, cyano, and alkylmercapto;

$R_4$ and $R_5$ are independently selected from the group consisting of hydrogen, lower-alkyl, aryl, and aryl lower-alkyl, or $R_4$ and $R_5$ together with the carbon atom to which they are attached form a 5- or 6-member saturated hydrocarbon ring;

$R_6$ is selected from the group consisting of hydrogen, lower-alkyl, aryl lower-alkyl, formyl, lower-alkyl carbonyl, and aryl carbonyl;

$R_7$ is selected from the group consisting of phenyl, thienyl, indolyl, indazolyl, benzo[b]furanyl, benzo[b]thiophenyl, and $R_8R_9$—N—; and $R_8$ is selected from the group consisting of 8-[1,2,3,4,-tetrahydroquinolinyl], pyridinyl, 3-quinolinyl, 2-naphthalinyl, 2-thiazolyl, 2-benzothiazolyl, 4-[2,1,3]benzothiadiazolyl, 2-(4,5,6,7-tetrahydrobenzo)thiazolyl, 7-(2,2-dimethyl-2,3-dihydrobenzo)furanyl, and phenyl;

$R_9$ is hydrogen or lower-alkyl;

$R_8R_9$—N— is a radical selected from the group consisting of 1-indolinyl, 1-(3,3-dimethylindolinyl), and 1-(1,2,3,4-tetrahydroquinolinyl); wherein the groups represented by $R_7$ other than $R_8R_9N$— may be unsubstituted or substituted with one or more substituents selected from the group consisting of lower-alkyl, lower-alkoxy, di-lower-alkylamino, and aryloxy, and the groups represented by $R_8$ and the radical $R_8R_9N$— may have one or more substituents selected from the group consisting of hydroxy, halogen, lower-alkyl, lower-alkoxy, amino, mono- or di-lower-alkylamino, lower-alkyl carbonyl, lower-alkoxy carbonyl, and aryloxy, wherein each aryloxy group may be unsubstituted or substituted with one or more substituents independently selected from the group consisting of lower-alkyl, lower-alkoxy, halogen, and trifluoromethyl with the proviso that, when $R_8$ is phenyl, said phenyl group contains at least one substituent;

wherein the symbol * represents an asymmetric carbon atom at position 6 which may be in the R or S configuration, and each lower-alkyl group contains from 1 to 6 carbon atoms.

13. The method according to claim 12, wherein $R_1$, $R_2$, $R_4$, and $R_5$ are individually hydrogen or methyl.

14. The method according to claim 12, wherein $R_3$ is selected from the group consisting of hydrogen, lower-alkyl, nitro, and amino.

15. The method according to claim 12, wherein $R_1$, $R_2$, and $R_3$ are hydrogen.

16. The method according to claim 12, wherein $R_6$ is hydrogen or lower-alkyl.

17. The method according to claim 12, wherein said compound of formula (1) comprises (R)-6-(2-benzothiazolyl)aminocarbonyl-5-methyl-4,5,6,7-tetrahydroimidazo[4,5-c]pyridine, and the pharmaceutically acceptable addition salts thereof.

18. The method according to claim 12, wherein $R_7$ is $R_8R_9$—N—, $R_8$ is phenyl containing one or more substituents independently selected from the group consisting of hydroxy, lower-alkyl carbonyl, and lower-alkoxy carbonyl, and $R_9$ is hydrogen.

19. The method according to claim 18, wherein said compound of formula (1) comprises (S)-6-(2-acetylphenyl)aminocarbonyl-5-methyl-4,5,6,7-tetrahydroimidazo[4,5-c]pyridine, and the pharmaceutically acceptable addition salts thereof.

20. The method according to claim 18, wherein said compound of formula (1) comprises (S)-6-(2-phenoxyphenyl)aminocarbonyl-5-methyl-4,5,6,7-tetrahydroimidazo[4,5-c]pyridine, and the pharmaceutically acceptable addition salts thereof.

21. The method according to claim 12, wherein $R_7$ is selected from the group consisting of phenyl, thienyl, indolyl, indazolyl, benzo[b]furanyl, and benzo[b]thiophenyl.

* * * * *